(12) United States Patent
Mackewitz et al.

(10) Patent No.: US 6,252,117 B1
(45) Date of Patent: Jun. 26, 2001

(54) PREPARATION OF PHOSPHABENZENE COMPOUNDS

(75) Inventors: Thomas Mackewitz, Mannheim; Michael Röper, Wachenheim; Bernhard Breit, Schriesheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/525,064

(22) Filed: Mar. 14, 2000

(30) Foreign Application Priority Data

Mar. 17, 1999 (DE) ............................................. 199 11 922

(51) Int. Cl.⁷ ...................................................... C07F 9/50
(52) U.S. Cl. .................................. 568/12; 562/30; 560/8; 564/16
(58) Field of Search ................................. 568/12; 560/8; 562/30, 35; 564/16

(56) References Cited

FOREIGN PATENT DOCUMENTS

| 16 18 668 | 2/1971 | (DE) . |
| 1 668 416 | 8/1971 | (DE) . |
| 16 68 413 | 8/1971 | (DE) . |
| 196 21 967 | 12/1997 | (DE) . |
| 197 43 197 | 4/1999 | (DE) . |
| WO 97/46507 | 12/1997 | (WO) . |
| WO 99/16774 | 4/1999 | (WO) . |

OTHER PUBLICATIONS

F. Lieb,, "Synthesne und Reaktionen von Phosphirinen, Untersuchungen zur Drstellung on Systemen mit Arsen-–Kohlenstoff–Doppelbindungen", Inaugural Thesis, Wurzburg, 1969, pp. 106–107.

*Primary Examiner*—Jean F. Vollano
(74) *Attorney, Agent, or Firm*—Keil & Weinkauf

(57) ABSTRACT

Phosphabenzene compounds of the formulae I and II

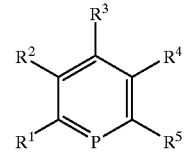

(I)

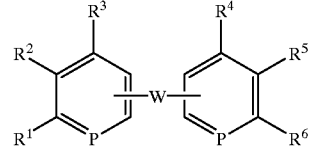

(II)

where $R^1$ to $R^6$ are identical or different and are, for example, hydrogen, are prepared by reacting corresponding pyrylium salts with $PH_3$ in the presence or absence of a solvent or diluent. The pyrylium salts are combined with $PH_3$ at above 0° C. and reacted at a temperature in the range from 0° C. to 200° C. and a pressure above 1 bar without addition of an acid catalyst or a base.

8 Claims, No Drawings

PREPARATION OF PHOSPHABENZENE COMPOUNDS

Phosphabenzene compounds can be used as ligands in transition metal complexes which are used in the hydroformylation of olefins.

DE-A 196 21 967 describes such complexes and processes for preparing them. In one process variant, 3,3'-bis(2,4,6-triphenylphosphabenzene)-1,1'-biphenyl can be prepared by reaction of the corresponding pyrylium salt with phosphine.

DE-A-16 18 668 describes a process for preparing substituted phosphabenzenes in which pyrylium salts are reacted with trishydroxymethylphosphine, tetrahydroxymethylphosphine chloride or tetrahydroxymethylphosphine hydroxide. The phosphine compounds are difficult to prepare and the process is not economical.

F. Lieb "Synthesen und Reaktionen von Phosphorinen, Untersuchungen zur Darstellung von Systemen mit Arsen-Kohlenstoff-Doppelbindungen", Inaugural Thesis, Würzburg, 1969, pages 106 and 107, describes a process for preparing 2,4,6-triphenylpyrylium tetrafluoroborate in n-butanol at −78° C., in which the reaction is carried out using $PH_3$ in the presence of a catalytic amount of acid (acetic anhydride/HBr) or of $CaCO_3$ which dissolves in the diluent, as base. After closing the reaction vessel, the reaction is carried out for 41 hours at 110° C. under autogenous pressure. The use of bases leads to formation of salts which necessitates further separation steps.

DE-A-16 68 416 describes phosphabenzenes and processes for preparing them by reaction of substituted pyrylium salts with phosphine. The reaction takes place in a glass autoclave in which phosphine is formed from phosphonium iodide only after closing the autoclave. Alternatively, phosphine is condensed in the reactor, which requires a temperature below the boiling point of phosphine, viz. −87° C. The reaction is then again carried out in an autoclave.

Carrying out the reaction under autogenous pressure has the disadvantage that the concentration of the reactants changes constantly and long reaction times are necessary. The introduction of $PH_3$ at −78° C. requires the use of appropriate cooling equipment. The process in a closed reaction vessel is difficult or impossible to control.

In DE-A-197 43 197, which has an earlier priority date but was not published before the priority date of the present application, some of the disadvantages described are avoided by a process in which pyrylium salts are reacted with phosphine in the presence of a catalytic amount of acid and in the presence or absence of a solvent or diluent. Here, the pyrylium salts are combined with phosphine at above 0° C. and reacted at from ≧0° C. to 200° C. and a pressure above 1 bar. The pyrylium salts are preferably combined with phosphine at ambient temperature and the resulting mixture is heated to a temperature in the range from 110 to 130° C. for the reaction. In the process described, catalytic amounts of acid are used. As acid catalysts, use is made of mineral acids such as HCl, HBr or HI. However, such free mineral acids can cause corrosion damage to metal autoclaves, pressure vessels or other reaction vessels. Furthermore, there is the risk of the desired product being contaminated with halide ions. When phosphabenzenes are used as cocatalysts, even traces of such contaminants can have an adverse effect on the catalyst properties.

It is an object of the present invention to provide a process for preparing phosphabenzene compounds which can be carried out economically and avoids the disadvantages of the known processes.

We have found that this object is achieved by a process for preparing phosphabenzene compounds of the formulae I and II

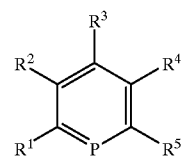

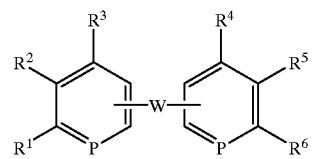

where $R^1$ to $R^6$ are, independently of one another, hydrogen, COOM, $SO_3M$, $NR_3X$, $NR_2$, OR, COOR or SR (where M=hydrogen, $NH_4$ or alkali metal, X=an anion, R=hydrogen or $C_{1-6}$-alkyl) or $C_{1-12}$-alkyl, $C_{6-12}$-aryl, $C_{7-12}$-aralkyl, $C_{7-12}$-alkaryl or $C_{3-6}$-heterocycloalkyl having from 1 to 3 heteroatoms which may be substituted by the above radicals, where two or more of the radicals may also be joined to form aliphatic or fused-on rings, and W is a bridge comprising a covalent bond, an oxo group, a sulfur group, an ammo group, a di-$C_{1-6}$-alkylsilicon group or a $C_{1-16}$-radical which may be a constituent of one or more linked cyclic or aromatic rings and may be interrupted by from 1 to 3 heteroatoms, where the o or m position of the phosphabenzene ring which is not bound to the bridge may in each case bear one of the radicals $R^1$ to $R^6$, by reacting corresponding pyrylium salts with $PH_3$ in the presence or absence of a solvent or diluent. In the process of the invention, the pyrylium salts are combined with $PH_3$ at above 0° C. and are reacted at a temperature in the range from 0° C. to 200° C. and a pressure above 1 bar without addition of an acid catalyst or a base. Not adding an acid catalyst or a base enables the process to be simplified and made more economical.

In one embodiment, 3,3'-bis(2,4,6-triphenylphosphabenzene)-1,1'-biphenyl is excepted.

It has surprisingly been found that phosphabenzene compounds of the above formulae can be obtained by reacting the corresponding pyrylium salts, i.e. compounds in which the phosphorus in the formulae I and II is replaced by $O^+$ and an appropriate counterion is present, with $PH_3$ if certain process conditions are adhered to. The pyrylium salts are readily available industrially or can be prepared by simple means. $PH_3$ is available industrially.

Even when the addition of an acid catalyst, in particular a mineral acid, is omitted, the process can be carried out in yields which are as high as before or even higher.

The free acid corresponding to the anion of the pyrylium salt can be separated from the product mixture obtained after the reaction by aqueous extraction and returned to the preparation of the pyrylium salt. The aqueous solution of, for example, tetrafluoroboric acid obtained in the extraction with water can, if desired, be isolated prior to recycling. The aqueous solution contains no mineral acid contamination.

The reaction is preferably carried out at a $PH_3$ partial pressure in the range from 0.1 to 100 bar, particularly preferably from 5 to 35 bar, in particular from 20 to 30 bar. The total pressure in the system depends on the solvent employed. The total pressure can be increased by injection of $PH_3$ or inert gas.

During the reaction, $PH_3$ is preferably passed into the reaction mixture in order to keep the $PH_3$ partial pressure essentially constant. This procedure allows a particularly economical and rapid reaction to form the desired phosphabenzene compounds. High product purities and conversions are achieved. The process of the present invention can be used reliably for many products. It can be carried out continuously or batchwise, preferably batchwise.

In a particularly advantageous process variant, the pyrylium salts are combined with $PH_3$ at ambient temperature, and the resulting mixture is reacted by heating to a temperature in the range from 60 to 140° C., preferably from 80 to 130° C.

The temperature of the reaction is particularly preferably from 100 to 120° C. The reaction is preferably carried out in an autoclave. In addition to $PH_3$, it is possible to use an inert gas by means of which the desired total pressure is set. However, preference is given to using only $PH_3$.

The reaction can be carried out in the presence or absence of a solvent or diluent. It is preferably carried out in the presence of a solvent or diluent. Suitable solvents and diluents are, for example, lower aliphatic alcohols such as methanol, ethanol, n-propanol, n-butanol, i-butanol, tert-butanol or pentanol isomers, preferably ethanol, propanol or butanols, in particular n-butanol.

After the reaction, the reaction mixture is preferably depressurized and, if desired, purged with an inert gas. The gases carried from the reaction mixture are cooled and passed through a separator to separate off unreacted $PH_3$ in liquid form and the $PH_3$ separated off is returned to the reaction.

A particularly economically and ecologically acceptable variant is thus a process in which $PH_3$ is pased into a reactor in which the reaction is carried out and the gas stream is passed via a further line to a cooler of any construction type in which the $PH_3$ is condensed out. In a downstream separator of any construction type, the $PH_3$ is then separated off and returned to the reaction, for example by means of a pump. In order to obtain a waste gas which is particularly low in $PH_3$, the use of a downstream second cooler and separator is advantageous. To free the reactor gas space and the equipment used completely of $PH_3$, which is advantageous owing to the toxicity of $PH_3$, a purge line for purging with an inert gas such as nitrogen should be provided. The purged gas should be passed through the combination of cooler and separator.

The time required for the reaction depends on the type of pyrylium salt. Depending on the pyrylium salt, the reaction is preferably carried out for from 1 to 4 hours. In the reaction in a solvent, the concentration of $PH_3$ in the solvent depends on the $PH_3$ partial pressure and the type of solvent; particularly when the reaction is carried out continuously, a high concentration of $PH_3$ in the solvent should be maintained.

To achieve high conversions in a short reaction time, the reaction is preferably carried out using high $PH_3$ pressures and continuous injection of further $PH_3$.

Many different pyrylium salts can be used in the process of the present invention. The process is generally not restricted to particular classes of compound. For example, the pyrylium salts can be ferrates, zincates, chlorides, borates, if desired substituted by a $C_{1-6}$-alkyl radical, triflates, trifluoroacetates or preferably tetrafluoroborates, perchlorates, hydrogensulfates, bromides, iodides or mixtures thereof. Preference is given to using tetrafluoroborates. The organic radical of the pyrylium salts used according to the present invention is described in more detail below by means of the phosphabenzene compounds prepared therefrom.

In the above compounds of the formula I, the radicals $R^1$ to $R^5$ are, independently of one another, hydrogen, COOM, $SO_3M$, $NR_3X$, $NR_2$, OR, COOR or SR (where M=hydrogen, $NH_4$ or an alkali metal, X=an anion, R=hydrogen or $C_{1-16}$-alkyl), or $C_{1-12}$-alkyl, $C_{6-12}$-aryl, $C_{7-12}$-aralkyl, $C_{7-12}$-alkaryl or $C_{3-6}$-heterocycloalkyl, where the alkyl, aryl, alkaryl and aralkyl radicals may be substituted by the abovementioned radicals and two or more of the radicals may be joined to form aliphatic or fused-on rings. The radicals $R^1$ to $R^5$ can be identical or different. $R^1$ to $R^5$ are preferably alkyl, aryl, alkaryl or aralkyl radicals which may be substituted.

If two or more of the radicals are joined to form aliphatic or fused-on rings, the compounds can be, for example, phosphanaphthalene or higher aromatic compounds. The radicals are preferably $C_{6-12}$-aryl radicals, particularly preferably phenyl radicals, or $C_{7-12}$-aralkyl radicals, particularly preferably benzyl radicals, or $C_{7-12}$-alkaryl radicals, particularly preferably 2- or 2,6-dialkylaryl radicals in the case of $R^1$ and $R^5$.

Particular preference is given to compounds of the formula I in which the 2, 6 and possibly 4 positions are substituted by substituted or unsubstituted phenyl radicals. In particular, phenyl radicals are present in all three positions. These radicals preferably have at most one further substituent. The substituent in the 4 position is preferably an acid or amine radical, possibly in salt form. Furthermore, a benzyl radical or 2-alkyl-substituted phenyl radical can be present in one or two or the 2,6 positions.

In the compounds of the formula II, $R^1$ to $R^6$ have the above meanings. W is a bridge comprising a covalent bond, an oxo group, a sulfur group, an amino group, a di-$C_{1-6}$-alkylsilicon group or a $C_{1-16}$-, preferably $C_{1-6}$-radical which may be a constituent of one or more linked cyclic or aromatic rings and may be interrupted by from 1 to 3 heteroatoms, where the o or m position of the phosphabenzene ring which is not bound to the bridge may in each case bear one of the radicals $R^1$ to $R^6$.

The bridge W may be, for example, a substituted or unsubstituted methylene group of the formula $CR^7R^8$, where $R^7$ and $R^8$ can be identical or different and are hydrogen or alkyl radicals having a total of from 1 to 15 carbon atoms or phenyl radicals, or else alkaryl or aralkyl radicals, as long as the radical has no more than 16 carbon atoms.

W can also be an oxa group (—O—), sulfur group (—S—), di-$C_{1-6}$-alkylsilicon group (—Si(alkyl)$_2$) or an amino group —$NR^9$—, where $R^9$ is $C_{1-6}$-alkyl, $C_{6-12}$-aryl, $C_{7-15}$-aralkyl, in particular benzyl.

W can comprise one or more linked cyclic or aromatic rings, particularly preferably one or two cyclic or aromatic rings. For example, W can be a o- or p-phenylene radical. Other suitable radicals are cycloalkyldiyl radicals, in particular cyclopentyldiyl and cyclohexyldiyl. Suitable aryldiyl groups are, for example, 1,1'-diphenyidiyl radicals, naphthyldiyl radicals, (diphenyl ether)diyl radicals, diphenylmethanediyl radicals, diphenylethanediyl radicals, diphenylpropanediyl radicals and ferrocenediyl radicals. Examples of suitable phosphabenzene compounds are listed in the abovementioned DE-A 196 21 97:

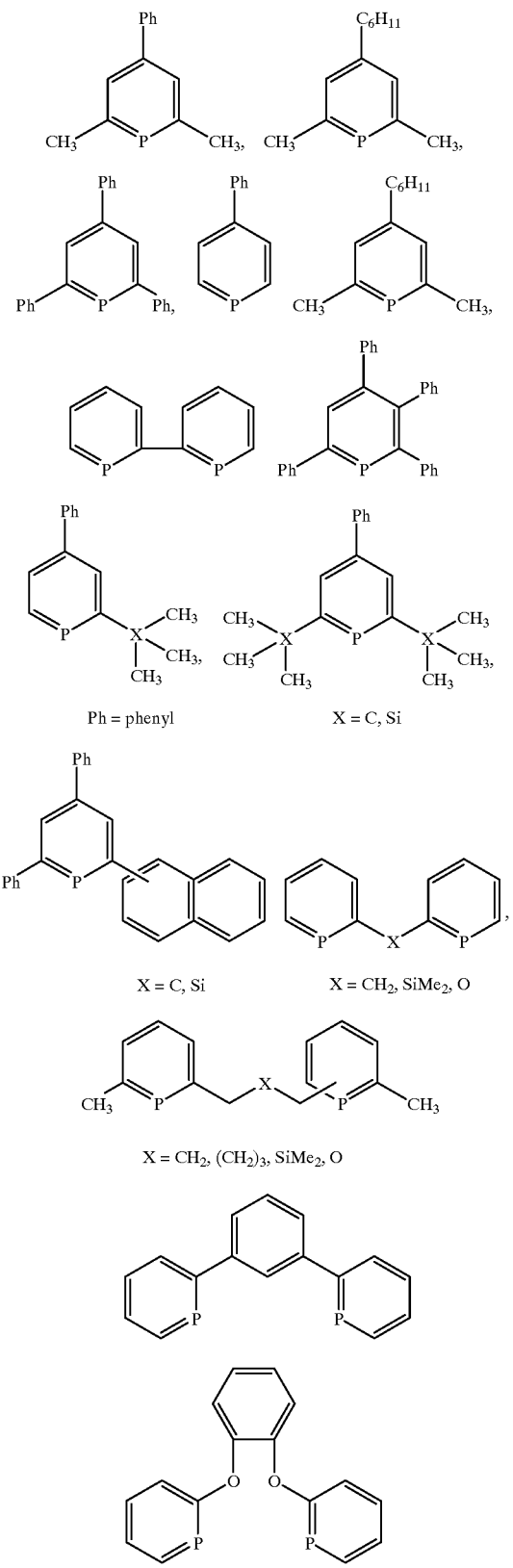

Ph = phenyl    X = C, Si

X = C, Si    X = CH₂, SiMe₂, O

X = CH₂, (CH₂)₃, SiMe₂, O

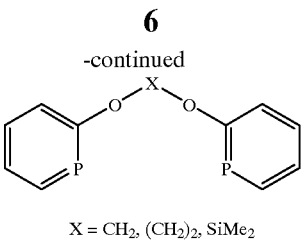

X = CH₂, (CH₂)₂, SiMe₂

The pyrylium salts used in the direct reaction with $PH_3$ can be obtained, for example, as described in Houben-Weyl, Hetarene II, Part 2, editor R. Kreher, Volume B7b, page 755 ff, Thieme Verlag, Stuttgart.

Further suitable phosphabenzene compounds are:

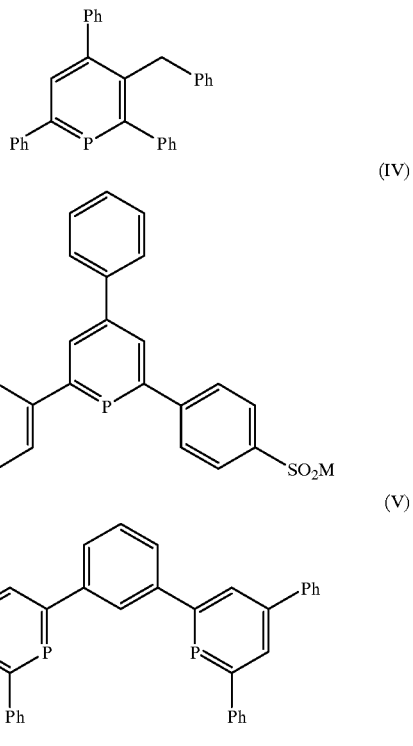

The compounds prepared according to the present invention can be used for the preparation of complexes of metals of transition group VIII of the Periodic Table of the Elements. Such complexes can be used as cocatalyst in hydroformylations. Suitable reaction conditions are described in DE-A 196 21 967 and in DE-A-197 43 197.

The invention is illustrated by the examples below:

EXAMPLES

Example 1

An autoclave (capacity: 300 ml; material: HC) was charged with 2,6-bis(2,4-dimethylphenyl)-4-phenylpyrylium tetafluoroborate (20 g) and n-butanol (150 ml) and pressurized with 5 bar of nitrogen. The gas space was subsequently flushed with $PH_3$. 5 bar of $PH_3$ were injected at room temperture and further $PH_3$ was injected until the pressure remained constant at 5 bar. The reaction mixture was heated to 110° C., and the solution was stirred vigorously using a sparging stirrer. Further PH$_3$ was injected to a pressure of 30 bar. During the reaction, the pressure in the reactor was kept at the desired pressure level by injection of further PH$_3$ via a pressure regulator. After a reaction time of 4 hours, the autoclave was cooled, vented, thoroughly purged with nitrogen while stirring and the reaction mixture was taken out. The autoclave product was evaporated to half its volume under reduced pressure The solid which precipitated was filtered off with suction, washed with n-butanol and subsequently dissolved in toluene. The toluene solution was then washed with water until the aqueous phase was neutral. After removal of the solvent and washing with a little n-pentane, the residue was dissolved in 250 ml of diethyl ether/methanol (3:2). The solution obtained was evaporated at 30° C. and 170 mbar until a white solid precipitated. The solid was filtered off with suction, washed with a little methanol and n-pentane and subsequently dried in a high vacuum. Yield: 8.9 g (53%).

General Experimental Description for Preparing Phosphabenzenes

All the following experiments (batchwise) were carried out in a 300 ml autoclave (material: HC). The autoclave was charged with pyrylium salt and a suitable solvent and pressurized with 5 bar of nitrogen. The gas space was subsequently flushed with PH$_3$. 5 bar of PH$_3$ were injected at room temperature and further PH$_3$ was injected until the pressure remained constant at 5 bar. The reaction mixture was heated to 110° C., and the solution was stirred vigorously using a sparging stirrer. Further PH$_3$ was injected to a pressure of 30 bar. During the reaction, the pressure in the reactor was kept at the desired pressure level by injection of further PH$_3$ via a pressure regulator. After a reaction time of 4 hours, the autoclave was cooled, vented, thoroughly purged with nitrogen while stirring and the reaction mixture was taken out. The autoclave product was then worked up as described below.

Example 2a

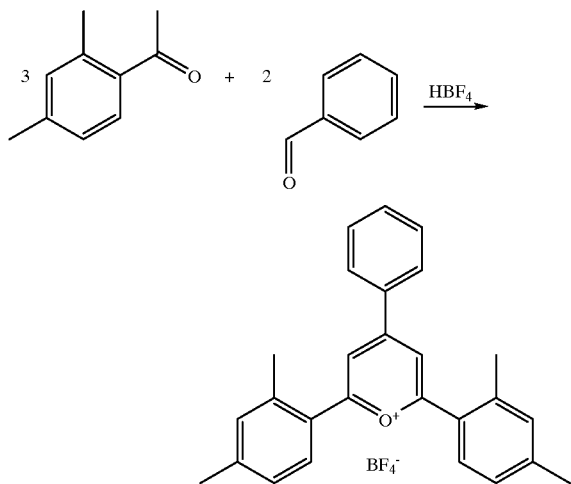

271 g (2.6 mol) of benzaldehyde and 542 g (3.7 mol) of 2,4-dimethylacetophenone were dissolved in 400 ml of 1,2-dichloroethane and heated to 80° C. 606 g (3.7 mol) of a 54% strength ether solution of tetrafluoroboric acid were slowly added dropwise while stirring. The mixture was subsequently stirred for another 4 hours at this temperature and then allowed to cool to room temperature. The volatile constituents of the deep red solution obtained were distilled off in a high vacuum with gentle heating. The residue was admixed with a toluene/water mixture (1:1). The orange-yellow solid which precipitated was filtered off, washed with water and toluene and dried in a high vacuum. To recrystallize the product, the solid was suspended in methanol and subsequently admixed with dichloromethane until a clear solution had been obtained. The solvent was distilled off in a high vacuum with gentle heating until solid again precipitated. The product was filtered off, washed in succession with methanol and n-pentane and subsequently dried in a high vacuum. Yield: 180 g (32%) of light-yellow solid.

Example 2b

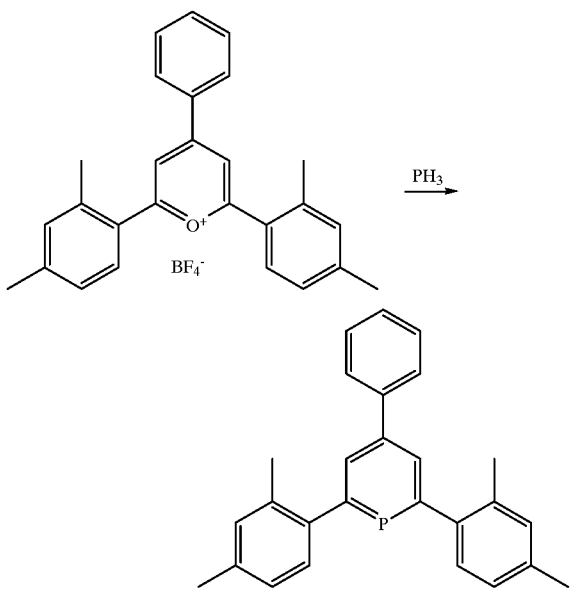

20 g (44 mmol) of 2,6-bis(2,4-dimethylphenyl)4-phenyl-pyrylium tetrafluoroborate in 150 ml of n-butanol were used. The autoclave product obtained after the reaction with PH$_3$ was evaporated to half its volume under reduced pressure. The solid which precipitated was filtered off with suction, washed with n-butanol and subsequently dissolved in toluene. The toluene solution was then washed with water until the aqueous phase was neutral. After removal of the solvent and washing with a little n-pentane, the residue was dissolved in 250 ml of diethyl ether/methanol (3:2). The solution obtained was evaporated at about 30° C. under reduced pressure until a solid precipitated. The solid was filtered off with suction, washed with a little methanol and n-pentane and subsequently dried in a high vacuum. Yield: 8.9 g (53%) of white solid.

Comparative Example 2b

The reaction was carried out using a method analogous to Example 2b, but with addition of 1 ml of a 30% strength HBr solution in acetic acid in the reaction with PH$_3$. The work-up was carried out using a method analogous to Example 2b. Yield: 8.9 g (53%).

Example 3a

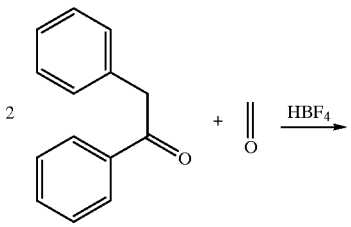

1st step: 40 g (0.20 mol) of deoxybenzoin were dissolved in 100 ml of ethanol. While stirring, 10.2 g (0.10 mol) of a 30% strength aqueous formaldehyde solution and subsequently 12.2 g (0.22 mol) of potassium hydroxide dissolved in a mixture of 7 ml of water and 150 ml of ethanol were added to the deoxybenzoin solution. After 2 hours, the solid which had precipitated was filtered off, washed with a little n-pentane and then dissolved in 300 ml of a mixture of dichloromethane/ethanol (2:1). The solvent was distilled off in a high vacuum with gentle heating until solid again precipitated. The product was filtered off, washed with n-pentane and subsequently dried in a high vacuum. Yield: 38 g (90%) of white solid.

2nd step: A solution of 0.70 g (2.7 mmol) of triphenylmethanol in 10 ml of acetic anhydride was added while stirring to a solution of 1.0 g (2.4 mmol) of 1,2,4,5-tetraphenyl-1,5-pentanedione in 20 ml of acetic anhydride. The reaction mixture was heated to 50° C. While stirring, 0.88 g (5.4 mol) of a 54% strength ether solution of tetrafluoroboric acid diluted with 5 ml of acetic anhydride was slowly added dropwise. The mixture was subsequently stirred for another 4 hours at 80° C., and then allowed to cool to room temperature. The solid formed after addition of 10 ml of diethyl ether was filtered off. The mother liquor was completely evaporated under reduced pressure and then admixed with 40 ml of a toluene/water mixture (1:1). The precipitated solid was filtered off and washed with a little n-pentane. To recrystallize the collected solids, they were suspended in about 30 ml of methanol and subsequently admixed with dichloromethane (about 50 ml) until a clear solution had been obtained. The solvent was distilled off in a high vacuum with gentle heating until solid again precipitated. The product was filtered off, washed with a little n-pentane and subsequently dried in a high vacuum. Yield: 0.6 g (53%) of light-yellow solid.

Example 3b

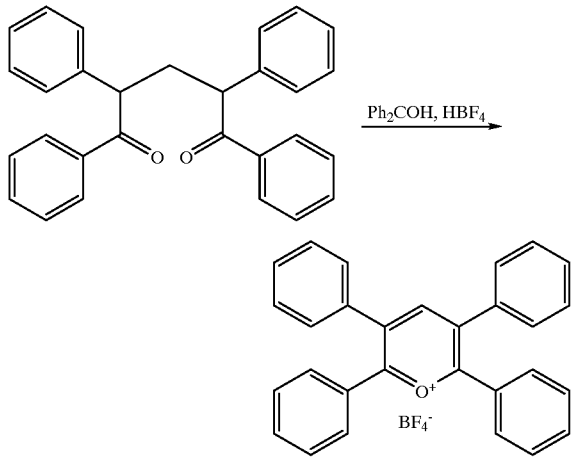

1.3 g (2.8 mmol) of 2,3,5,6-tetraphenylpyrylium tetrafluoroborate in 150 ml of n-butanol were used. The autoclave product obtained after the reaction with $PH_3$ was evaporated to one-third of its volume at about 80° C. under reduced pressure. The solid which precipitated was filtered off with suction, washed with n-butanol and subsequently dissolved in toluene. The toluene solution was then washed with water until the aqueous phase was neutral. After removal of the solvent, the residue was dissolved in a mixture of dichloromethane and methanol. The solution obtained was evaporated at about 50° C. under reduced pressure until a solid precipitated. The solid was filtered off with suction, washed with a little n-pentane and subsequently dried in a high vacuum. Yield: 0.8 g (71%) of white solid.

Comparative Example 3b

The reaction was carried out by a method analogous to Example 3b using 1.0 g (2.1 mmol) of 2,3,5,6-tetraphenylpyrylium tetrafluoroborate as starting material, but with addition of 1 ml of a 30% strength HBr solution in acetic acid in the reaction with $PH_3$. The work-up was carried out using a method analogous to Example 3b. Yield: 0.3 g (35%).

Example 4

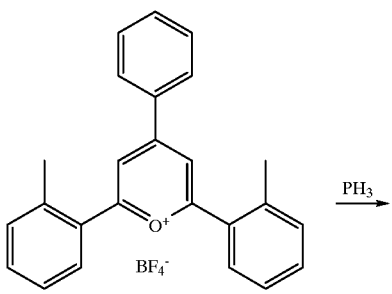

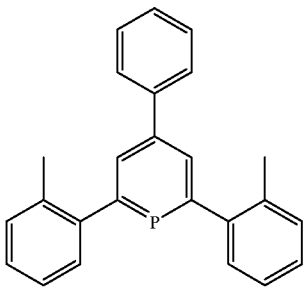

The reaction was carried out twice using 15 g (35 mmol) of 2,6-bis(2-methylphenyl)-4-phenylpyrylium tetrafluoroborate in 150 ml of n-butanol each time. The two autoclave products obtained after the reaction with PH$_3$ were combined and evaporated to about 50 ml at about 80° C. under reduced pressure. The solid which precipitated was filtered off with suction, washed with n-pentane and subsequently dissolved in toluene. The toluene solution was then washed with water until the aqueous phase was neutral. After removal of the solvent, the residue was suspended in methanol and then admixed with dichloromethane until the solid had completely dissolved. The solution obtained was evaporated at about 40° C. under reduced pressure until a solid precipitated. The solid was filtered off with suction, washed with a little n-pentane and subsequently dried in a high vacuum. Yield: 15.6 g (63%) of white solid.

Example 5

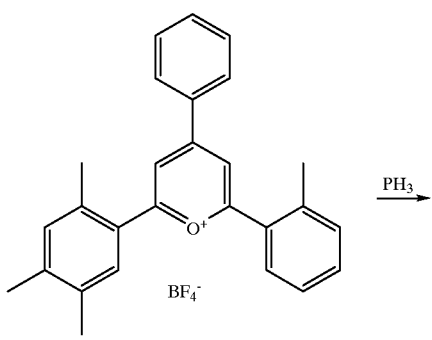

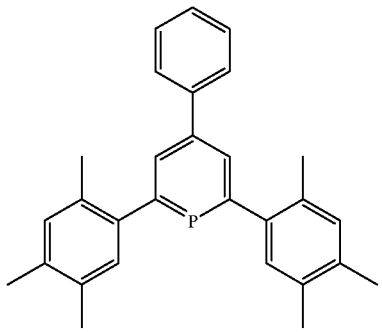

2.1 g (4.4 mmol) of 2,6-bis(2,4,5-trimethylphenyl)-4-phenylpyrylium tetrafluoroborate in 150 ml of n-butanol were used. The autoclave product obtained after the reaction with PH$_3$ was evaporated to about 50 ml at about 80° C. under reduced pressure. The solid which precipitated was filtered off with suction, washed with n-pentane and subsequently dissolved in toluene. The toluene solution was then washed with water until the aqueous phase was neutral. After removal of the solvent and washing with a little n-pentane, the residue was dissolved in dichloromethane. The solution obtained was diluted with methanol and then evaporated at 30° C. under reduced pressure until a solid precipitated. The solid was filtered off with suction, washed with a little n-pentane and subsequently dried in a high vacuum. Yield: 0.8 g (45%) of light-yellow solid.

Example 6

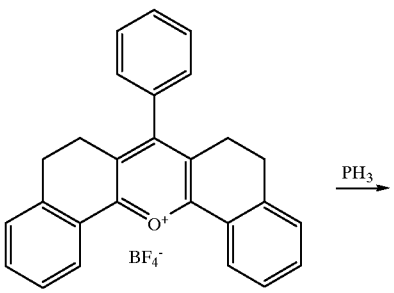

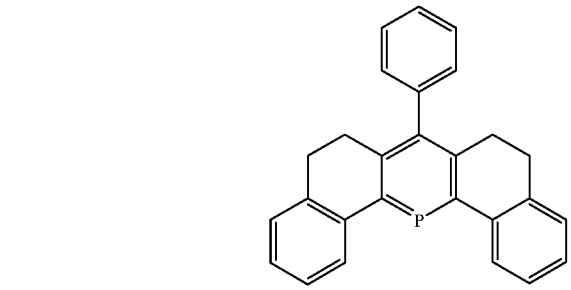

3.5 g (7.8 mmol) of 10-phenyl-1,2,7,8-dibenzo-3,4,5,6-tetrahydro-9-oxoniaanthracene tetrafluoroborate in 150 ml of ethanol were used. The autoclave product obtained after the reaction with PH$_3$ was freed of volatile constituents at about 80° C. under reduced pressure. The orange residue was suspended in about 200 ml of warm toluene and immediately filtered through a frit. The toluene solution was then washed with water until the aqueous phase was neutral. After removal of the solvent at 80° C. under reduced pressure, the solid which remained was dissolved in about 30 ml of methanol and about 200 ml of dichloromethane and then slowly evaporated at 50° C. under reduced pressure until a solid precipitated. The solid was filtered off with suction, washed with a little n-pentane and subsequently dried in a high vacuum. Yield: 0.7 g (24%) of light-yellow solid.

We claim:

1. A process for preparing phosphabenzene compounds of the formula I and II

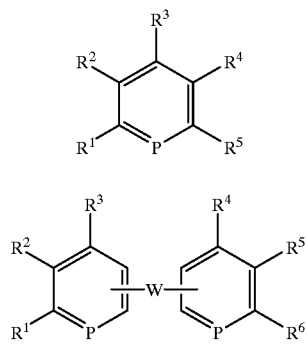

where $R^1$ to $R^6$ are, independently of one another, the radicals hydrogen, COOM, $SO_3M$, $NR_3X$, $NR_2$, OR, COOR or SR (where M=hydrogen, $NH_4$ or alkali metal, X=an anion, R=hydrogen or $C_{1-6}$-alkyl); or are the substituents $C_{1-12}$-alkyl, $C_{6-12}$-aryl, $C_{7-12}$-aralkyl, $C_{7-12}$-alkaryl or $C_{3-6}$-heterocycloalkyl having from 1 to 3 heteroatoms, which are optionally substituted by the above radicals or by above substituents, where two or more of the above substituents are optionally joined to form aliphatic fused-on rings, and W is a bridge selected from a covalent bond, an oxo group, a sulfur group, an amino group, a di-$C_{1-6}$-alkylsilicon group or a $C_{1-16}$-radical which is optionally a constituent of one or more linked cyclic or aromatic rings and the $C_{1-16}$radical is optionally interrupted by from 1 to 3 heteroatoms, where the o or m position of the phosphabenzene ring which is not bound to the bridge is optionally substituted in each case with one of the radicals $R^1$ to $R^6$, by reacting the corresponding pyrylium salts with $PH_3$ in the presence or absence of a solvent or diluent, wherein the pyrylium salts are combined with $PH_3$ at above 0° C. and are reacted at a temperature in the range from 0° C. to 200° C. and a pressure above 1 bar without addition of an acid catalyst or a base, and said $PH_3$ is passed into the reaction mixture during the reaction in order to keep the $PH_3$ partial pressure essentially constant.

2. The process of claim 1, wherein the reaction is carried out at a $PH_3$ partial pressure in the range from 0.1 to 100 bar.

3. The process of claim 1, wherein the reaction is carried out at a pressure of from 5 to 25 bar.

4. The process of claim 1, wherein the pyrylium salts are combined with $PH_3$ at ambient temperature and the mixture obtained in this way is reacted by heating to a temperature in the range from 110 to 130° C.

5. The process of claim 1, wherein the $R^1$ to $R^6$ substituents on compounds of the formulae I and II are phenyl substituents or benzyl substituents which are optionally substituted by $SO_3M$.

6. The process of claim 1, wherein the pyrylium salts are tetrafluoroborates, perchlorates, hydrogensulfates, bromides, iodides or mixtures thereof.

7. The process of claim 1, wherein, after the reaction, the reaction mixture is depressurized and is optionally purged with an inert gas and the gases from the reaction mixture are cooled and passed through a separator to separate off unreacted $PH_3$ in liquid form and the $PH_3$ separated off is returned to the reaction.

8. The process of claim 1, wherein the free acid corresponding to the anion of the pyrylium salt is separated from the resulting product mixture by aqueous extraction and is used in the preparation of the pyrylium salt.

* * * * *